(12) United States Patent
Kawai et al.

(10) Patent No.: US 12,044,811 B2
(45) Date of Patent: Jul. 23, 2024

(54) CONTROL APPARATUS, CONTROL METHOD, RADIOGRAPHIC IMAGING SYSTEM, AND STORAGE MEDIUM

(71) Applicant: CANON KABUSHIKI KAISHA, Tokyo (JP)

(72) Inventors: Masaya Kawai, Kanagawa (JP);
Hironori Yamashita, Kanagawa (JP);
Tomohiro Kawanishi, Tokyo (JP);
Keiko Uehara, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 274 days.

(21) Appl. No.: 17/736,901

(22) Filed: May 4, 2022

(65) Prior Publication Data

US 2022/0365227 A1 Nov. 17, 2022

(30) Foreign Application Priority Data

May 11, 2021 (JP) ................................. 2021-080613

(51) Int. Cl.
*G01T 1/17* (2006.01)
*A61B 6/00* (2006.01)
*G01N 23/04* (2018.01)

(52) U.S. Cl.
CPC ................. *G01T 1/17* (2013.01); *A61B 6/54* (2013.01); *G01N 23/04* (2013.01)

(58) Field of Classification Search
None
See application file for complete search history.

(56) References Cited

U.S. PATENT DOCUMENTS

| 10,485,505 | B2* | 11/2019 | Yamada | A61B 6/566 |
| 2005/0169425 | A1* | 8/2005 | Takasawa | A61B 6/547 378/97 |
| 2013/0058454 | A1* | 3/2013 | Kuwabara | A61B 6/548 378/62 |
| 2018/0125441 | A1* | 5/2018 | Arima | G16H 30/20 |
| 2020/0305823 | A1* | 10/2020 | Asai | H05G 1/60 |

FOREIGN PATENT DOCUMENTS

| JP | 2009031682 A * | 2/2009 |
| JP | 5675537 B2 | 2/2015 |
| JP | 5706278 B2 | 4/2015 |

* cited by examiner

*Primary Examiner* — Marcus H Taningco
(74) *Attorney, Agent, or Firm* — Canon U.S.A., Inc. IP Division

(57) ABSTRACT

A control apparatus includes a detection unit configured to detect switching between a plurality of radiation detection apparatuses, each of the plurality of radiation detection apparatuses being configured to capture a radiographic image through detection of radiation and including a plurality of receptor fields for performing automatic exposure control, an acquisition unit configured to acquire information regarding one of the plurality of radiation detection apparatuses to be used for image capturing in a case where switching to the one of the plurality of radiation detection apparatuses has been detected, and a selection unit configured to select one or more of the plurality of receptor fields of the one of the plurality of radiation detection apparatuses to be used for the image capturing based on the acquired information and information of a subject as an image capturing target and information of a part of the subject to be imaged.

14 Claims, 10 Drawing Sheets

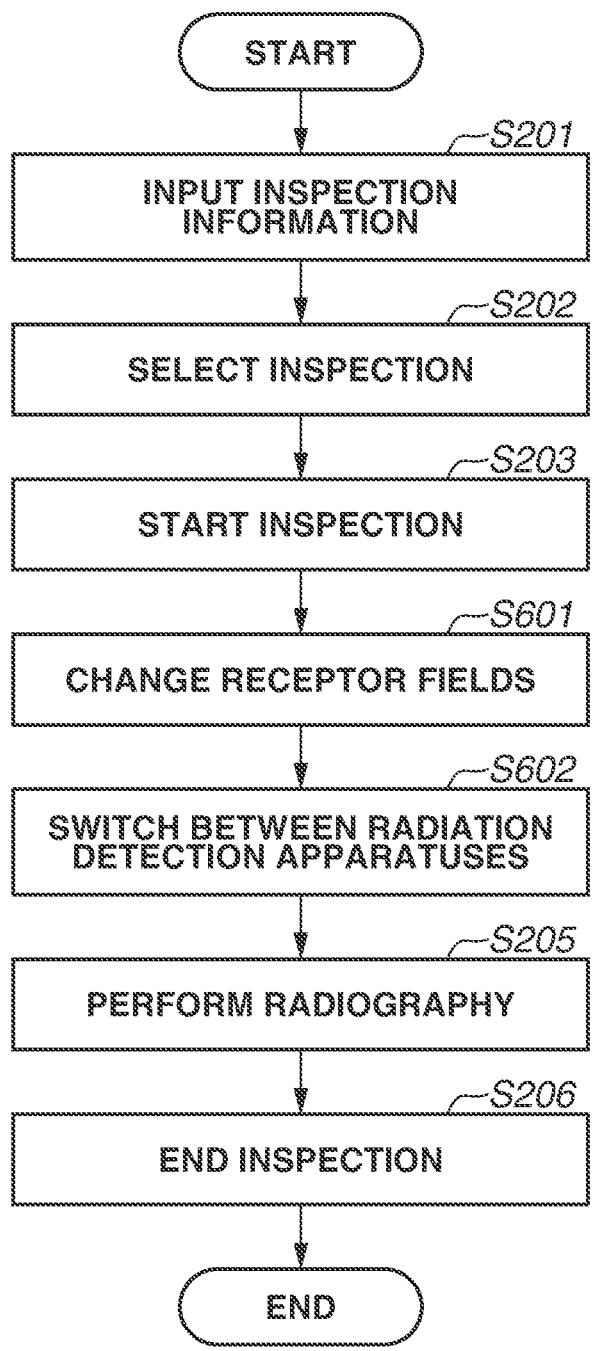

CONTROL APPARATUS, CONTROL METHOD, RADIOGRAPHIC IMAGING SYSTEM, AND STORAGE MEDIUM

BACKGROUND OF THE INVENTION

Field of the Disclosure

The present disclosure relates to a control apparatus, a control method, a radiographic imaging system, and a storage medium.

Description of the Related Art

Radiographic imaging apparatuses with sensor panels to detect radiation such as X-rays are widely used in the fields of industry, medicine, and others. In recent years, functional expansions of radiographic imaging apparatuses have been studied. For example, an embedded function of monitoring radiation emitted from a radiation source has been studied. This function makes it possible to detect, for example, a timing at which radiation from the radiation source has been started, a timing at which irradiation is to be stopped, and an amount of radiation or an accumulated amount of radiation. Automatic exposure control (AEC) can also be performed by detecting the accumulated amount of radiation having passed through a subject and stopping the radiation from the radiation source at a point of time when the detected accumulated amount of radiation has reached a proper amount. In general, for automatic exposure control using a flat panel detector (FPD), a plate-like AEC sensor separate from the FPD is interposed between the subject and the FPD. The AEC sensor measures the amount of radiation having passed through the subject in one to five predetermined radiation detection areas (receptor fields) where radiation is monitored, and performs a control to stop X-ray radiation when the amount of radiation reaches a predetermined dose of radiation.

In a case of radiographic imaging using a separate AEC sensor, a radiographic imaging is executed in an erect or supine position because the FPD and AEC sensor are difficult to transport. If the FPD is equipped with the AEC function, the FPD will be transportable like a conventional FPD, so that the subject can assume a position other than an erect or supine position at the time of AEC radiographic imaging. In addition, it will also be possible to switch among a plurality of FPDs equipped with the AEC function different in size and the number of receptor fields in accordance with use applications. Japanese Patent No. 5675537 and Japanese Patent No. 5706278 discuss switching technique for a conventional stationary AEC sensor.

Japanese Patent No. 5675537 and Japanese Patent No. 5706278 describe inventions for solving an issue of, in a case where a stationary AEC sensor is changed to a new AEC sensor, applying settings for the AEC sensor before the change to the AEC sensor after the change.

When a plurality of FPDs equipped having the AEC function is used, the FPDs may have different sizes or receptor field positions from each other. It may be necessary to change the positions of the receptor fields after switching between the AEC sensors, which may increase the burden on the operator.

SUMMARY

In view of the above-described issue, an object of the present disclosure is to reduce the burden on the operator and improve the usability of a system according to the present invention.

The present disclosure is not limited to the above-mentioned object. It can be regarded as another object of the present disclosure to provide advantageous effects, which cannot be obtained by the conventional techniques, derived from the configurations described below in relation to the embodiments for carrying out the invention.

According to an aspect of the present invention, a control apparatus includes a detection unit configured to detect switching between a plurality of radiation detection apparatuses, each of the plurality of radiation detection apparatuses being configured to capture a radiographic image through detection of radiation and including a plurality of receptor fields for performing automatic exposure control, an acquisition unit configured to acquire information regarding one of the plurality of radiation detection apparatuses to be used for image capturing in a case where switching to the one of the plurality of radiation detection apparatuses has been detected, and a selection unit configured to select one or more of the plurality of receptor fields of the one of the plurality of radiation detection apparatuses to be used for the image capturing based on the acquired information and information of a subject as an image capturing target and information of a part of the subject to be imaged.

Further features of the present invention will become apparent from the following description of exemplary embodiments with reference to the attached drawings.

BRIEF DESCRIPTION OF THE DRAWINGS

FIG. 6 is a flowchart illustrating an example of an imaging process according to a second exemplary embodiment.

DESCRIPTION OF THE EMBODIMENTS

Hereinafter, exemplary embodiments of the present invention will be described with reference to the accompanying drawings. The following exemplary embodiments are not intended to limit the present invention defined in the claims, and not all of combinations of features described in the exemplary embodiments are necessarily essential to the solutions of the present invention. In the following exemplary embodiments and the claims, examples of a radiation include X-rays, α-rays, β-rays, γ-rays, and various particle beams.

Figure 1:
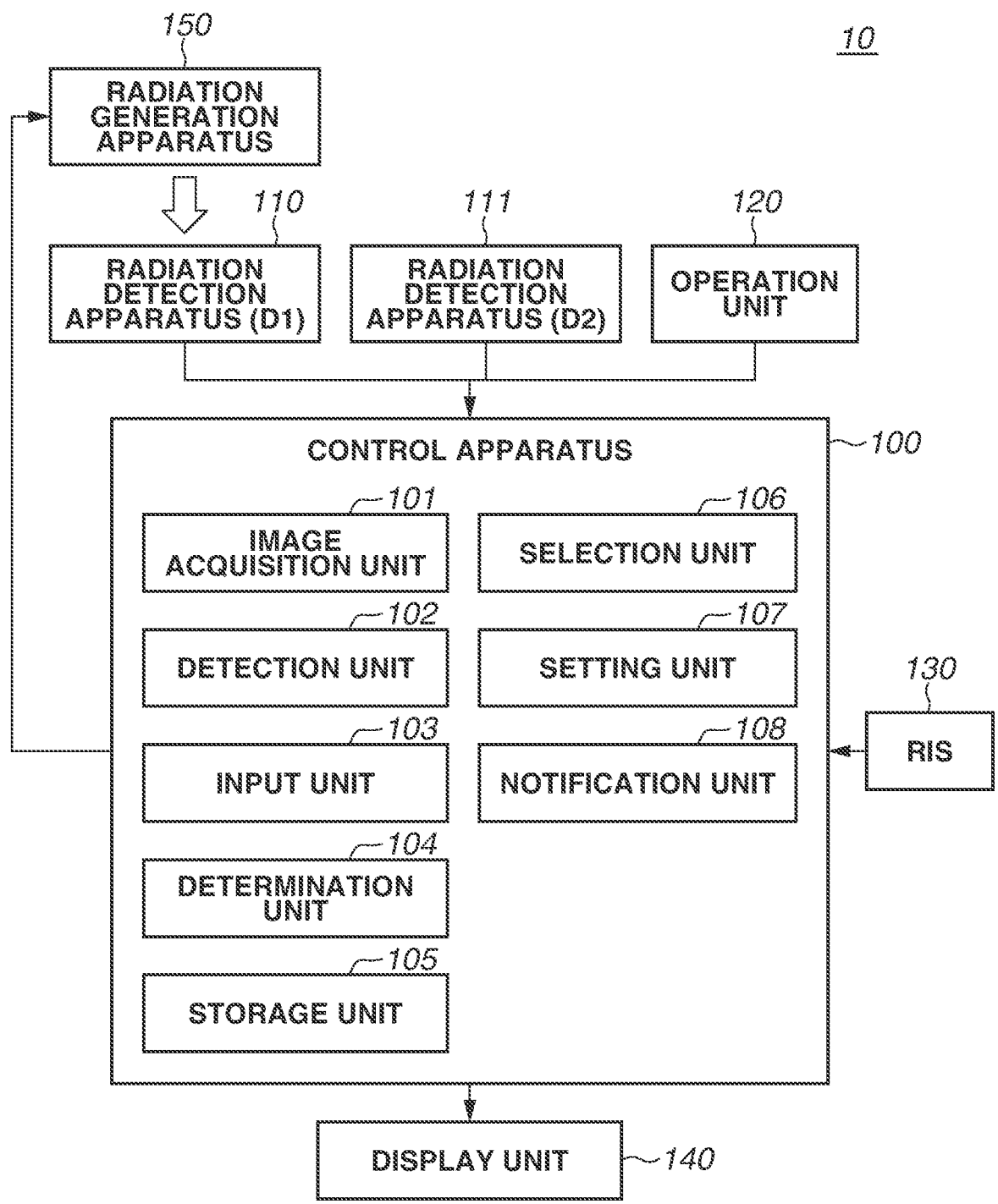
FIG. 1 is a block diagram illustrating a configuration example of a radiographic imaging system according to a first exemplary embodiment.

FIG. 1 is a diagram illustrating a configuration of a radiographic imaging system according to a first exemplary embodiment of the present invention. A radiographic imaging system 10 includes a control apparatus 100, a radiation detection apparatus (D1) 110, a radiation detection apparatus (D2) 111, an operation unit 120, a radiology information system (RIS) 130, a display unit 140, and a radiation generation apparatus 150.

The radiation detection apparatus (D1) 110 detects radiation having been emitted from the radiation generation apparatus 150 and passed through a subject (not illustrated), and outputs image data according to the radiation. The image data can also be referred to as a medical image or a radiographic image. The radiation detection apparatus (D1) 110 detects the radiation having passed through the subject, as electric charge corresponding to the dose of transmitted radiation. As a component that converts the radiation into electric charge, a case using the radiation detection apparatus (D1) 110 will be described here. The radiation detection apparatus (D1) 110 may employ a direct-conversion sensor, such as amorphous selenium (a-Se) sensor, that converts radiation directly into electric charge, or an indirect-conversion sensor using a scintillator such as cesium iodide (CsI) that converts radiation into visible light and a photoelectric conversion element such as amorphous silicon (a-Si). The radiation detection apparatus (D1) 110 generates digital image data by performing analog to digital (A/D) conversion on the detected electric charge of analog data, and outputs the digital image data to the control apparatus 100.

The control apparatus 100 is connected to the RIS 130 to which an inspection order (inspection information) is input and the display unit 140. The control apparatus 100 is also capable of controlling radiographic imaging using the radiation detection apparatus (D1) 110, the radiation detection apparatus (D2) 111, and the radiation generation apparatus 150. The control apparatus 100 is connected to the radiation generation apparatus 150 and the radiation detection apparatus (D1) 110 via, for example, wired or wireless networks or dedicated lines. The radiation detection apparatus (D1) 110 generates image data based on the radiation generated by the radiation generation apparatus 150 and outputs the generated image data to the control apparatus 100.

The control apparatus 100 is capable of performing display control to output images to the display unit 140 or provide a graphical user interface using the display unit 140, while controlling operations of the radiation detection apparatus (D1) 110.

The control apparatus 100 has one or more processors and memories, and implements functional components described below by causing the processors to execute programs stored in the memories. However, some or all of the functional components may be implemented by hardware, such as a dedicated integrated circuit, as long as the hardware performs similar functions.

The control apparatus 100 controls the radiographic imaging system 10 to perform X-ray radiographic imaging with cooperation between the radiation generation apparatus 150 and the radiation detection apparatus (D1) 110. That is, the control apparatus 100 communicates with the radiation generation apparatus 150 and the radiation detection apparatus (D1) 110 to perform operation control of these apparatuses.

The control apparatus 100 includes, as functional components, an image acquisition unit 101, a detection unit 102, an input unit 103, a determination unit 104, a storage unit 105, a selection unit 106, and a setting unit 107.

The image acquisition unit 101 acquires image data from the radiation detection apparatus (D1) 110 or the radiation detection apparatus (D2) 111, which has been used for radiographic imaging.

The detection unit 102 detects switching, such as switching from the radiation detection apparatus (D1) 110 to the radiation detection apparatus (D2) 111, of the radiation detection apparatus used by the operator. Upon detection of the switching, the detection unit 102 requests the determination unit 104 to determine whether appropriate receptor fields are set for the pre-switching radiation detection apparatus and the post-switching radiation detection apparatus. The receptor field here refers to, as described above, a radiation detection area where radiation is monitored, which is predetermined in order to measure the dose of radiation having passed through the subject and perform a control to stop X-ray radiation when a predetermined amount of dose is reached. This makes it possible to detect a timing at which radiation from the radiation source has been started, a timing at which radiation is to be stopped, and an amount of radiation or an accumulated amount of radiation. In addition, automatic exposure control (AEC) can be performed by detecting the accumulated amount of radiation having passed through the subject and stopping the radiation from the radiation source at a point of time when the detected accumulated amount of radiation has reached a proper amount.

The input unit 103 accepts an input of inspection information manually input by the operator through the operation unit 120. The input unit 103 also accepts a selection from the operation unit 120 regarding the inspection information acquired from the RIS 130. The input unit 103 sets the radiographic imaging target based on the selected inspection information, depending on the operation input by the operator selecting any one of a plurality of pieces of inspection information through the operation unit 120.

The determination unit 104 determines whether appropriate receptor fields are set for the pre-change radiation detection apparatus and the post-change radiation detection apparatus. Specifically, for example, the determination unit 104 determines whether appropriate receptor fields are set by determining an inclusive relationship between a subject area decided using information on the subject and information on a part of the subject to be imaged and a receptor field area decided using information regarding the radiation detection apparatus and the information on the part to be imaged. Specific process performed by the determination unit 104 will be described below.

The storage unit 105 holds master data that is inherent catalog information regarding each of the radiation detection apparatus (D1) 110 and the radiation detection apparatus (D2) 111. In the present exemplary embodiment, two types of radiation detection apparatuses, i.e., the radiation detection apparatus (D1) 110 and the radiation detection apparatus (D2) 111, are used. Alternatively, three or more types of radiation detection apparatuses may be connected and their respective specific catalog information may be held.

The selection unit 106 selects the receptor fields to be used in the post-change radiation detection apparatus based on the result of determination by the determination unit 104.

Based on the result of determination by the determination unit 104, the setting unit 107 disables receptor fields if there is no receptor field that is appropriately settable the post-change radiation detection apparatus.

If there is no available receptor field, a notification unit 108 notifies the operator, accordingly.

Figure 4:
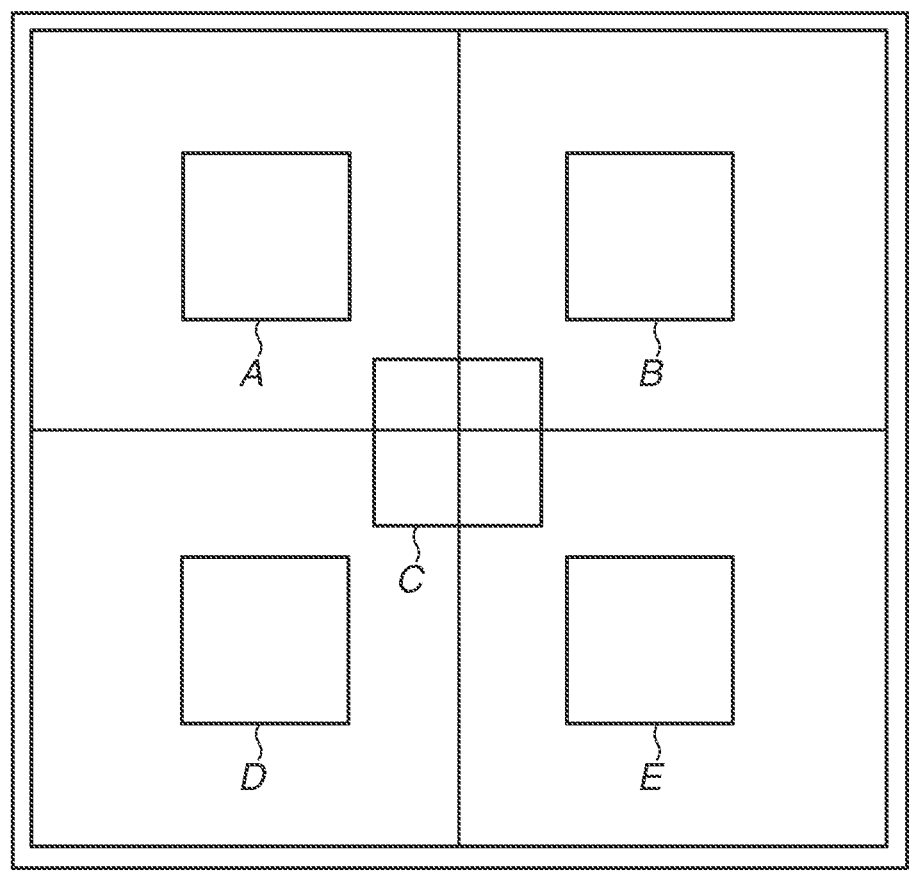
FIG. 4 is a diagram illustrating an example of a receptor field layout according to the first exemplary embodiment.

As a characteristic configuration of the first exemplary embodiment, two types of radiation detection apparatuses are used, i.e., the radiation detection apparatus (D1) 110 and the radiation detection apparatus (D2) 111, the apparatuses being different in performance each other. Specifically, the radiation detection apparatus (D1) 110 includes five receptor fields at positions A to E as illustrated in FIG. 4. The radiation detection apparatus (D2) 111 includes nine receptor fields AA to AI as illustrated in FIGS. 5A to 5E. The radiation detection apparatus (D2) 111 is smaller in size than the radiation detection apparatus (D1) 110. The rectangular receptor fields of the radiation detection apparatus (D2) 111 are also smaller in size than those of the radiation detection apparatus (D1) 110. FIGS. 4 and 5A to 5E illustrate mere examples and the present invention is not limited thereto.

Next, a specific example of a flow of imaging process by the radiographic imaging system 10 according to the first exemplary embodiment will be described.

Figure 2:
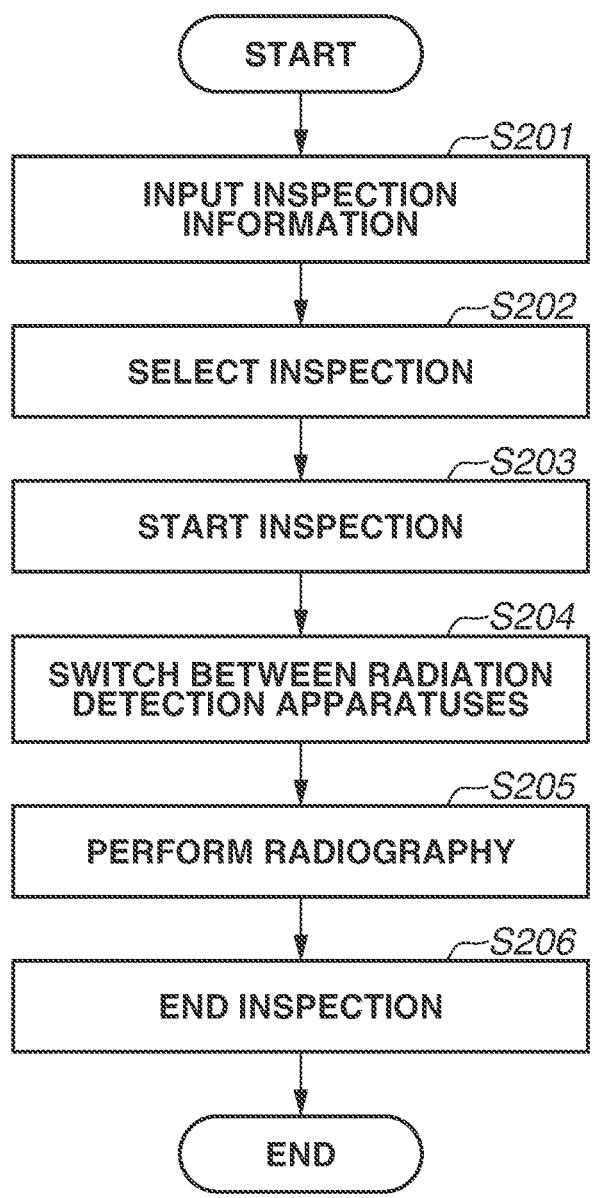
FIG. 2 is a flowchart illustrating an example of an imaging process according to the first exemplary embodiment.

FIG. 2 is a flowchart describing the processing flow of the imaging process.

(S201: Inputting Inspection Information)

In step S201, the input unit 103 selects, as a method for inputting inspection information, use of inspection information received from the RIS 130 or manual input of inspection information by the operator through the operation unit 120, thereby inputting the inspection information by using the selected method.

If the input unit 103 selects the manual input as the method for inputting inspection information, the processing proceeds to step S203 after the input of the inspection information. In contrast, if the input unit 103 selects the use of inspection information received from the RIS 130, the processing proceeds to step S202.

Specific inspection information for inputting inspection information include, for example, information for identifying and characterizing a person, such as a patient's ID, name, gender, age, height, and weight. This is equally applied to the cases between the manual input of inspection information and the use of inspection information from the RIS 130. As to the characteristic personal information, numeric information may not be used and text, graphics, or icons indicating a general body size may be selected.

(S202: Selecting Inspection)

In step S202, the input unit 103 selects and sets one of the pieces of inspection information received from the RIS 130, as an inspection target. For example, the input unit 103 sets the imaging target based on the selected inspection information in response to an operation input of selecting any one of the plurality of pieces of inspection information displayed in a list form. The operation input is performed by the operator through the operation unit 120. In the following description of the exemplary embodiment, a chest is set as the part to be imaged.

(S203: Starting Inspection)

In step S203, the inspection is started under the control of the control apparatus 100. For imaging of the imaging target set based on the inspection information manually input in step S201 or the inspection information selected in step S202, the control apparatus 100 transmits a signal to the radiation detection apparatus (D1) 110 to cause the radiation detection apparatus (D1) 110 to transition to the ready state.

Based on the signal transmitted from the control apparatus 100, if no bias voltage is applied to a two-dimensional imaging element, the radiation detection apparatus (D1) 110 controls a bias power source with a main control circuit to apply a bias voltage to the two-dimensional imaging element. Thereafter, the radiation detection apparatus (D1) 110 performs an initialization process of reading image signals from the pixel array using a drive circuit in order to read accumulated dark current signals from the pixels.

After the end of the initialization, the radiation detection apparatus (D1) 110 transmits state information indicating that the radiation detection apparatus (D1) 110 is in a state (imaging-enabled state) ready to capture a radiographic image to the control apparatus 100. When the radiation detection apparatus (D1) 110 enters the imaging-enabled state, the radiation detection apparatus (D1) 110 can capture a radiographic image.

In step S203, the operator performs positioning of the radiation detection apparatus (D1) 110 with respect to the part of the subject to be imaged until the radiation detection apparatus (D1) 110 can perform imaging.

If the body size of the subject is small, the inappropriate-size radiation detection apparatus may be switched to the appropriate-size radiation detection apparatus. Specifically, the radiation detection apparatus (D1) 110 is set as default to use the receptor fields A and B illustrated in FIG. 4 for chest radiography, but if the subject is a child or a baby, the receptor fields may be larger than the part of the subject to be imaged, and thus appropriate radiography may not be performed. The following steps will be described for a case where it is necessary to switch between the radiation detection apparatuses. As an example, the following steps will be described for a case where the subject as an imaging target has a small body size, such as a child.

(S204: Switching Between Radiation Detection Apparatuses)

In step S204, the operator changes to the radiation detection apparatus of a size suited to the subject. Specifically, the operator changes to the radiation detection apparatus (D2) 111 that has small receptor fields and small spacing between the receptor fields. The size of the radiation detection apparatus (D2) 111 allows the chest radiography using the receptor fields AA and AC illustrated in FIGS. 5A and 5B. If the subject is an infant, the radiography can be allowed by using only the receptor field AB illustrated in FIGS. 5A and 5B.

Switching between the detectors may be made by an operation from the operation unit or by a physical switch provided in the radiation detection apparatus. Alternatively, switching from the radiation detection apparatus (D1) 110 to the radiation detection apparatus (D2) 111 may be made by any method other than the above-described methods.

Hereinafter, description will be provided as to a case of switching from the radiation detection apparatus (D1) 110 illustrated in FIG. 4 to the radiation detection apparatus (D2) 111 illustrated in FIGS. 5A to 5E as an example. When the switching between the radiation detection apparatuses takes place, the detection unit 102 of the control apparatus 100 detects the switching between the radiation detection apparatuses. At this time, the detection unit 102 detects that the pre-switching apparatus is the radiation detection apparatus (D1) 110 and the post-switching apparatus is the radiation detection apparatus (D2) 111. The detection unit 102 requests the determination unit 104 to perform processing based on the detected information.

The determination unit 104 determines the receptor fields by using the patient information input in step S201, the part-to-be-imaged information selected at the inspection selection in step S202, the information on the pre-switching radiation detection apparatus (D1) 110, and the information on the post-switching radiation detection apparatus (D2) 111.

Figure 3:
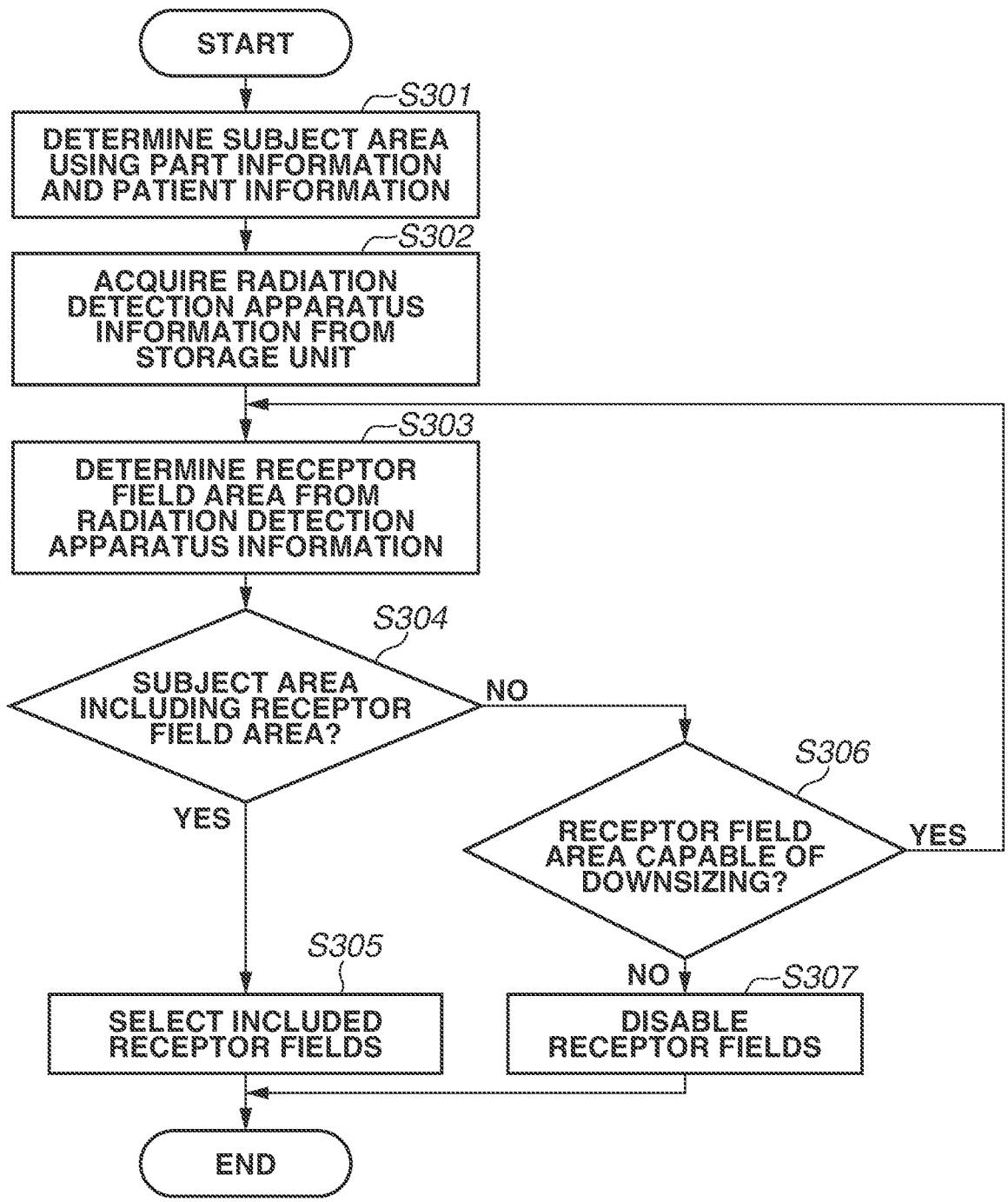
FIG. 3 is a flowchart related to a determination unit according to the first exemplary embodiment.

The detailed description will now be described with reference to the flowchart in FIG. 3.

(S301: Determining a Subject Area Using the Part Information and Patient Information)

In step S301, the determination unit 104 determines a subject area based on the patient information input through the input unit 103 and the part information selected at the start of the inspection.

The subject area is a real-size area of the subject to be actually imaged, which is expressed in a shape of a rectangle based on, for example, the patient information, such as the patient's height, weight, gender, and age input at the start of the inspection and the part of the subject to be imaged. For example, the subject area can be expressed as a rectangular area 501 illustrated in FIG. 5D. The rectangular area 501 is determined based on, for example, statistical information. Specifically, in a case of performing, for example, a chest radiography as described in the present exemplary embodiment, a typical chest circumference size can be acquired from the body height with reference to statistical information in a clothing size chart or the like, and a rough chest size can be calculated from the statistical information. Alternatively, the rectangular area 501 may be calculated based on past information of the same patient or may be determined using an optical camera (not illustrated). The subject area may be identified (inferred) by an optical camera using a rule-based table or a learned model having undergone machine learning. The learned model here is referred to as a machine learning model that have undergone learning in advance with appropriate learning data according to a machine learning algorithm, such as deep learning using a support vector machine or a neural network. The learned model is not limited to a model not subjected to further learning but may be subjected to additional learning. The learning data is formed of one or more groups of pairs of input data and output data (correct-answer data). The learning model according to the present exemplary embodiment has undergone learning with output data (data for identifying the subject area) corresponding to input data (data on a plurality of feature amounts detected from a radiographic image), according to an arbitrary learning algorithm. In the present exemplary embodiment, for example, the subject area is inferred by inputting an optical image captured by an optical camera to the learned model having undergone learning so as to identify a plurality of pixels in the optical image as a first class group (e.g., the subject area and the other areas). The above-described methods for determining the rectangular area 501 are mere examples and are not exclusive methods.

(S302: Acquiring Radiation Detection Apparatus Information from Storage Unit)

In step S302, the determination unit 104 acquires the information of the post-switching radiation detection apparatus (D2) 111 detected by the detection unit 102, from the storage unit 105. The acquired information of the radiation detection apparatus (D2) 111 includes, for example, the overall size of the radiation detection apparatus, the number of the receptor fields, the positions of the receptor fields, the horizontal and vertical sizes of a rectangle usable as a receptor field, and the distance between two different receptor fields. The information will be used in the subsequent steps.

(S303: Determining Receptor Fields from Radiation Detection Apparatus Information)

In step S303, the determination unit 104 determines a receptor field area for determining receptor fields to be used in the post-switching radiation detection apparatus (D2) 111.

The receptor field area is a real-size area including a plurality of receptor fields expressed in the shape of a circumscribed rectangle. The form of expression of the receptor field area is not limited to a circumscribed rectangle but may be a circle, such as a precise circle or an ellipse, or any other shape.

Figure 5E:
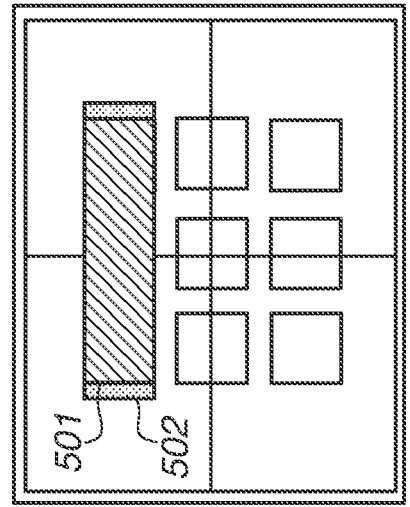
FIGS. 5A to 5E are diagrams illustrating examples of receptor field layouts according to the first exemplary embodiment.
Figure 5B:
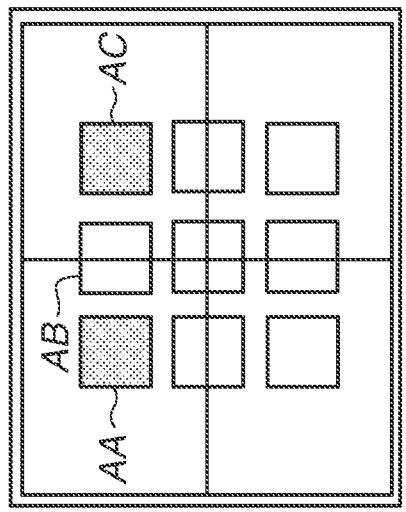

The receptor field area is determined based on the subject part to be imaged and the default settings of receptor fields of the radiation detection apparatus (D2) 111. Specifically, if the part to be imaged is a chest, the default settings of the receptor fields are the receptor fields AA and AC, for example, as illustrated in FIG. 5B. If the part to be imaged is an abdomen, the default settings is, for example, the receptor field AE.

Figure 5D:
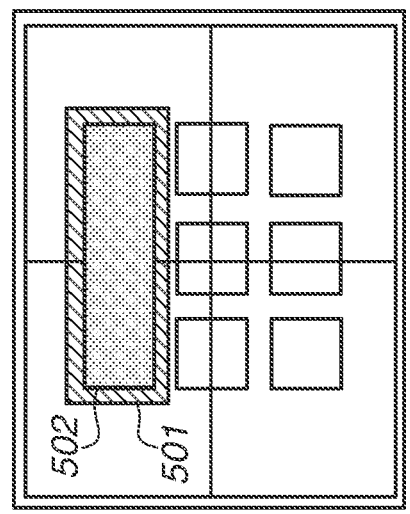
Figure 5A:
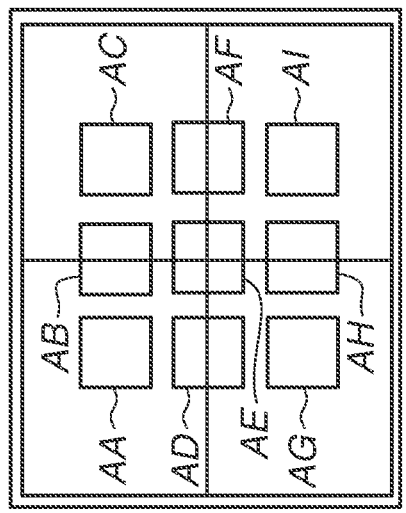
Figure 5C:
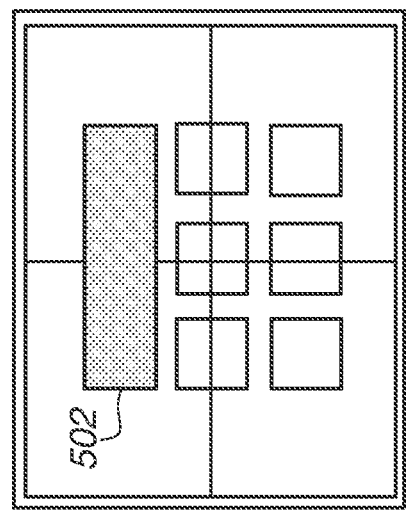

In the case where the part to be imaged is a chest, the receptor field area is a circumscribed rectangular area 502 including the receptor fields AA, AB, and AC as illustrated in FIG. 5C, and the actual size of the rectangle is calculated based on the information acquired in step S302.

(S304: Determining Whether Subject Area Includes Receptor Field Area)

In step S304, the determination unit 104 compares the subject area 501 determined in step S301 and the receptor field area 502 determined in step S303 to determine an inclusive relationship between the subject area 501 and the receptor field area 502. Specifically, the determination unit 104 overlaps, for example, the respective upper left apexes of the subject area 501 and the receptor field area 502 to determine whether the receptor field area 502 is included in the subject area 501 in the right and downward directions. The method for determining whether the subject area 501 includes the receptor field area 502 is not limited to the above. For example, the determination may be made by overlapping the respective centers of the rectangular areas. If the subject area 501 fully includes the receptor field area 502 as illustrated in FIG. 5D (YES in step S304), the processing proceeds to step S305. In contrast, if the subject area 501 partially includes the receptor field area 502 or does not include the receptor field area 502 at all (NO in step S304), the processing proceeds to step S306.

(S305: Selecting Included Receptor Fields)

In step S305, the selection unit 106 selects the receptor fields included in the receptor field area 502 compared in step S304, as the receptor fields to be used in the post-change radiation detection apparatus (D2) 111. Specifically, in this example, the selection unit 106 selects the default settings of receptor fields AA and AC where the part to be imaged is a chest, as the receptor fields. That is, the selection unit 106 corresponds to one example of selection unit that selects the receptor fields set for the part to be imaged, if the determination unit determines that the subject field fully includes the receptor field area in the determination result obtained by the determination unit.

(S306: Determining Whether Receptor Field Area Can Be Downsized)

In step S306, the determination unit 104 determines whether the receptor field area 502 compared in step S304 includes a plurality of receptor fields and the receptor field area 502 can be downsized by decreasing the number of the target receptor fields.

Specifically, the receptor field area 502 compared in step S304 includes the receptor fields AA, AB, and AC in the radiation detection apparatus (D2) 111 illustrated in FIGS. 5A to 5E, and thus the receptor field area 502 that is a circumscribed rectangle of receptor fields can be downsized by enabling only the receptor field AB, for example.

In the case of downsizing the receptor field area 502, it is preferred to select the receptor field as close to the center of the receptor field area 502 as possible. This is because, if a receptor field at an end of the radiation detection apparatus is selected, the receptor field may extend off the subject at the time of positioning, so that direct X-ray radiation may be stopped at an unexpected time. Thus, selecting the receptor field close to the center can reduce the possibility of the stoppage of the radiation at an unexpected time.

However, it is not necessarily required to select the receptor field close to the center to downsize the receptor field area 502. Any receptor field may be selected as long as the selection of receptor fields can reduce the possibility of radiation being stopped at an unexpected time.

In step S306, if it determined that the receptor field area 502 can be downsized (YES in step S306), the processing proceeds to step S303, and the determination unit 104 determines the receptor field area 502 again and performs the subsequent steps pone more time. That is, if determining that the subject area 501 does not include a part of the receptor field area 502, the determination unit 104 further determines the inclusive relationship between the receptor field area 502 having been downsized so as to eliminate the part not included and the subject area 501. If the receptor field area 502 cannot be downsized (NO in step S306), the processing proceeds to step S307.

(S307: Disabling Receptor Fields)

In step S307, since the size of a rectangle usable as a receptor field of the radiation detection apparatus (D2) 111 may be larger than the subject and there is a possibility that intended radiography cannot be performed, the setting unit 107 determines that there is no available receptor field and disables all the receptor fields. That is, if the receptor field area 502 cannot be downsized so as to eliminate the part not included in the subject area 501, the setting unit 107 disables the receptor fields.

At this time, the notification unit 108 may notify the operator that there is no available receptor field, on the display unit 140.

(S205: Performing Radiography)

In step S205, the control apparatus 100 captures a radiographic image through cooperation of the radiation generation apparatus 150 and the radiation detection apparatus (D2) 111. A drive circuit in the radiation detection apparatus (D1) 110 reads, by a read circuit, an image signal obtained through detection of the emitted radiation, and generates image data. Thereafter, the radiation detection apparatus (D1) 110 transmits the image data to the control apparatus 100. The image acquisition unit 101 of the control apparatus 100 acquires the image data transmitted from the radiation detection apparatus (D1) 110.

(S206: Ending Inspection)

In step S206, the inspection is ended by the operator's input operation.

As described above, the series of processing steps is executed by the radiographic imaging system 10.

According to the above description, the radiographic imaging system 10 according to the first exemplary embodiment can reduce the burden on the operator and improve the usability of the radiographic imaging system 10 by selecting appropriate receptor fields when switching from a radiation detection apparatus to another radiation detection apparatus.

In a second exemplary embodiment, description will be provided to a case of changing, after the start of an inspection, receptor fields before switching between radiation detection apparatuses. Description of parts overlapping the first exemplary embodiment will be omitted.

FIG. 6 is a flowchart describing a flow of radiographic imaging process in the present exemplary embodiment. In the flowchart of FIG. 6, steps S201 to S203, S205, and S206 are similar to those in the flowchart of FIG. 2, and the change of receptor fields (step S601) and the switching between radiation detection apparatuses (step S602) are different from the flowchart illustrated in FIG. 2.

(S601: Changing Receptor Fields)

In step S601 of FIG. 6, the operator changes the settings of the receptor fields of a radiation detection apparatus (D1) through an operation unit 120 after the start of the inspection.

(S602: Switching Between Radiation Detection Apparatuses)

In step S602, as in the first exemplary embodiment, the operator changes to the radiation detection apparatus of a size suited to the subject. Differently from the first exemplary embodiment, the settings of the receptor fields is changed in advance in step S601.

Figure 7:
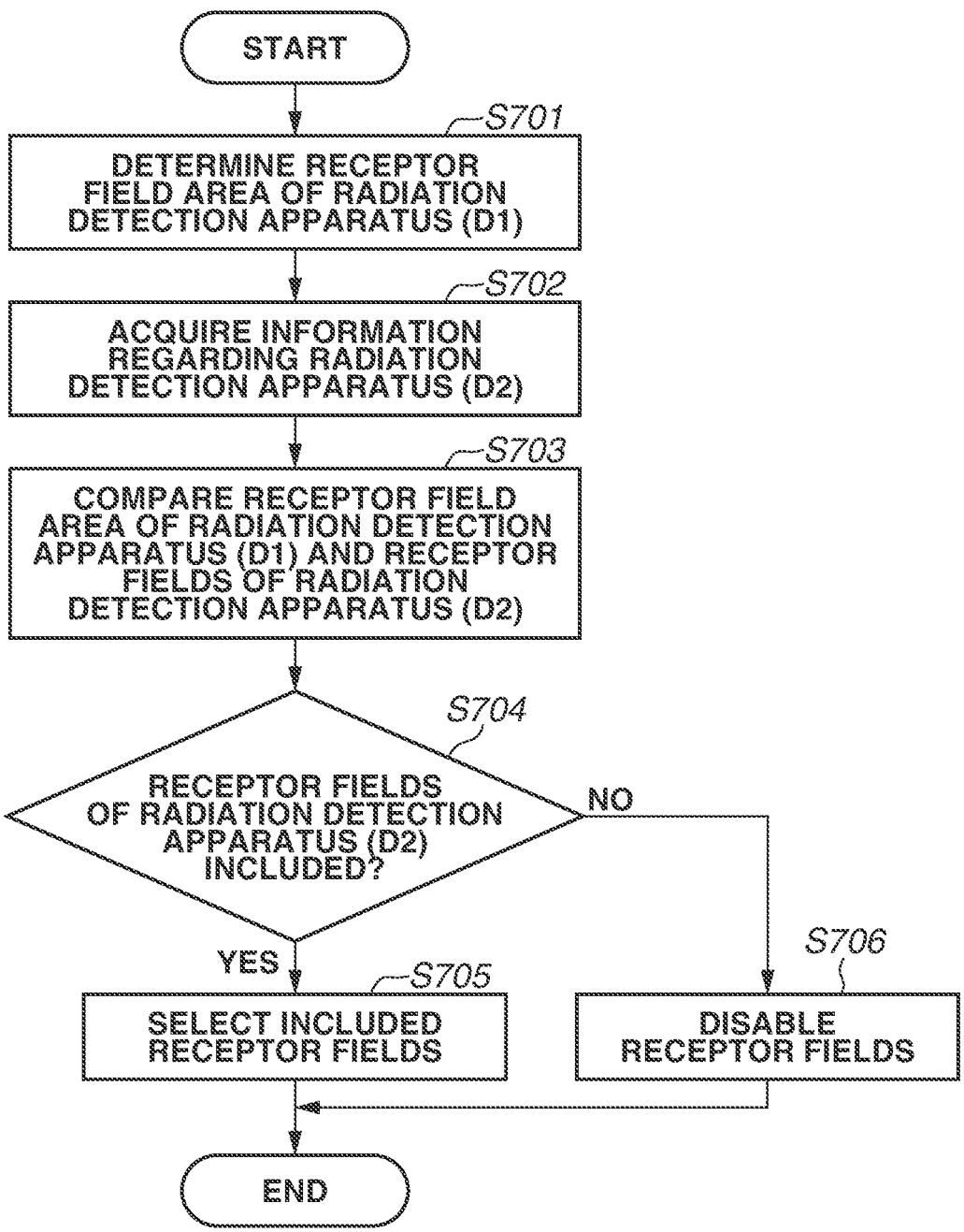
FIG. 7 is a flowchart related to a determination unit according to the second exemplary embodiment.

The detailed description will be provided with reference to the flowchart of FIG. 7.

(S701: Determining a Receptor Field Area of Radiation Detection Apparatus (D1))

Figure 8:
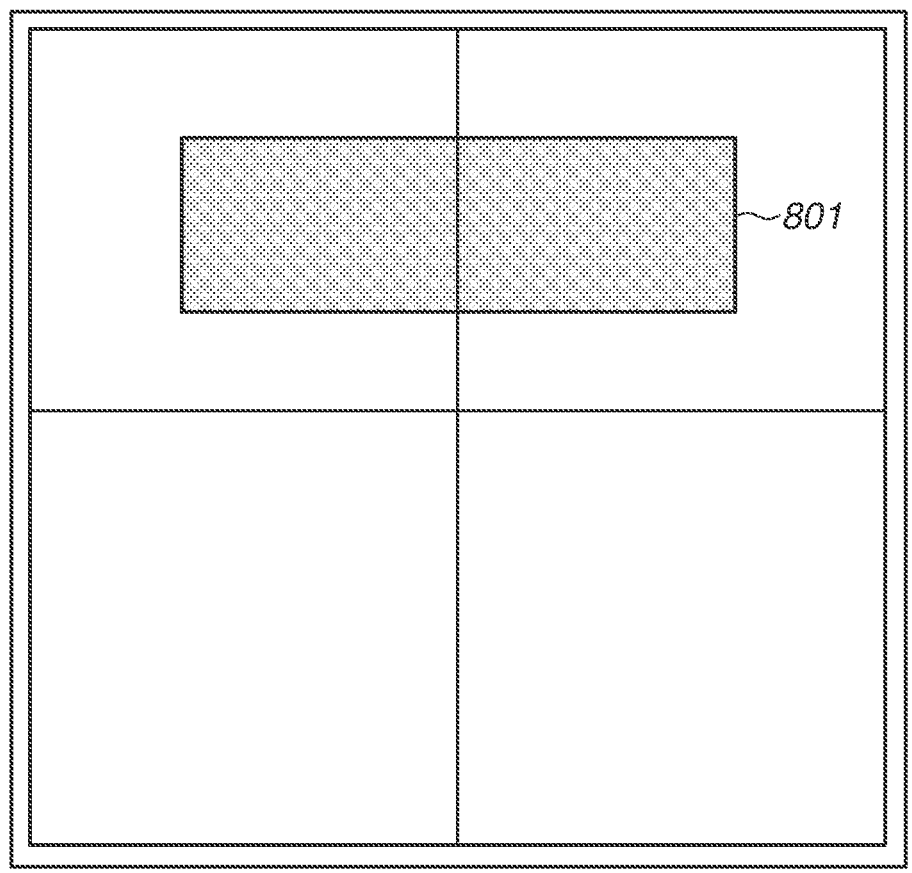
FIG. 8 is a schematic diagram illustrating determination of a receptor field area according to the second exemplary embodiment.

In step S701, a circumscribed rectangle including the changed receptor fields for determining a receptor field area in the radiation detection apparatus (D1) is generated. This circumscribed rectangle is set as a receptor field area. That is, in the present exemplary embodiment, the receptor field area is determined based on the information set for a first radiographic imaging apparatus through the operation unit 120. Specifically, if the receptor field A and the receptor field B in FIG. 4 are set in step S601, a receptor field area 801 illustrated in FIG. 8 is set as a receptor field area.

(S702: Acquiring Information Regarding Radiation detection apparatus (D2))

In step S702, the information regarding a radiation detection apparatus (D2) 111 is acquired from a storage unit 105.

(S703: Comparing Receptor Field Area of Radiation Detection Apparatus (D1) and Receptor Fields of Radiation Detection Apparatus (D2))

Figure 9:
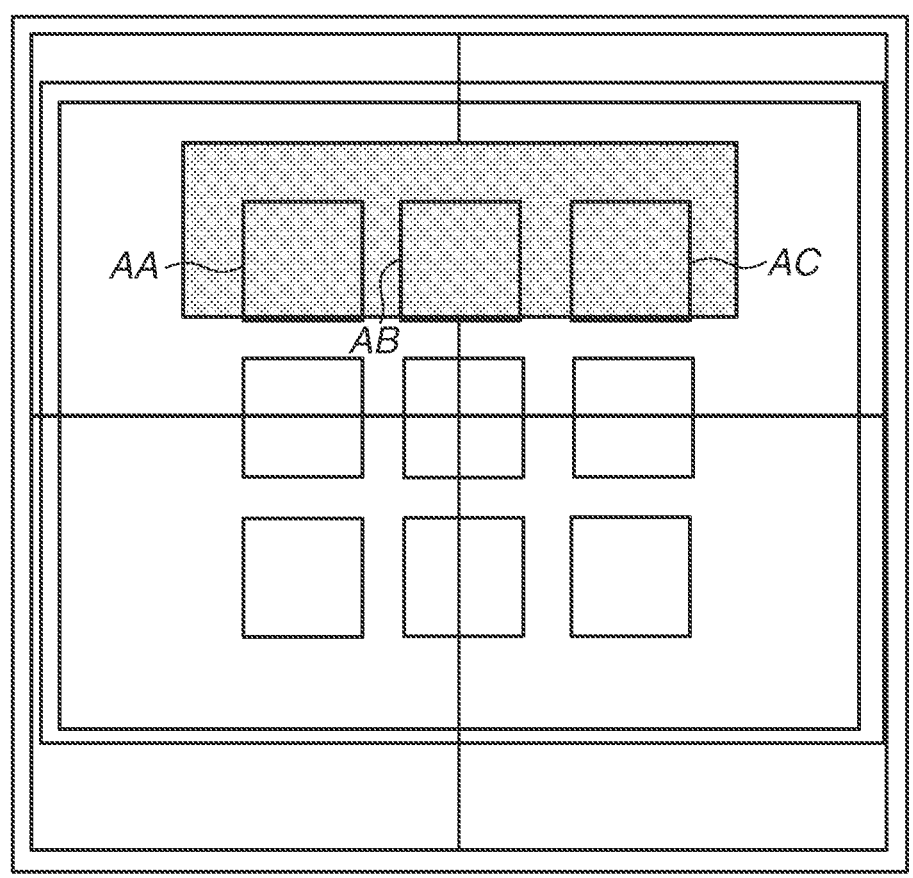
FIG. 9 is a schematic diagram illustrating comparison between a receptor field area and a radiation detection apparatus according to the second exemplary embodiment.

In step S703, the receptor field area of the radiation detection apparatus (D1) 110 determined in step S701 is compared with the receptor fields of the radiation detection apparatus (D2) 111. Specifically, the center of the radiation detection apparatus (D1) 110 and the center of the radiation detection apparatus (D2) 111 are overlapped as illustrated in FIG. 9.

(S704: Determining Whether Receptor Fields of (D2) Are Included)

In step S704, it is determined whether the receptor fields of the radiation detection apparatus (D2) 111 are included in the overlapped receptor field area determined on the radiation detection apparatus (D1) 110. In FIG. 9, the receptor fields AA, AB, and AC are included in the receptor field area. If the receptor fields are included (YES in step S704), the processing proceeds to step S705. If the receptor fields are not included (NO in step S704), the processing proceeds to step S706.

(S705: Selecting Included Receptor Fields)

In step S705, the included receptor fields are set as receptor fields of the post-switching radiation detection apparatus (D2) 111.

(S706: Disabling Receptor Fields)

In step S706, since no receptor field are included in the post-switching radiation detection apparatus (D2) 111, the receptor fields are disabled. Alternatively, default receptor fields with a combination of the radiation detection apparatus (D2) 111 and the part information may be adopted.

At this time, it may be notified to the operator that there is no available receptor field, on the display unit 140.

As described above, the series of steps is executed by a radiographic imaging system 10 according to the second exemplary embodiment.

According to the above description, the radiographic imaging system 10 according to the second exemplary embodiment can reduce the burden on the operator and improve the usability of the system by transferring the receptor field settings and selecting appropriate receptor fields at the time of switching between the radiation detection apparatuses even after the change of the receptor fields.

In relation to a third exemplary embodiment, description will be provided as to a case where, if a more appropriate radiation detection apparatus and receptor field settings are present in comparison to a combination of the radiation detection apparatus and receptor field settings at the start of the inspection, the operator is notified accordingly. Description of parts overlapping the first exemplary embodiment will be omitted.

Figure 10:
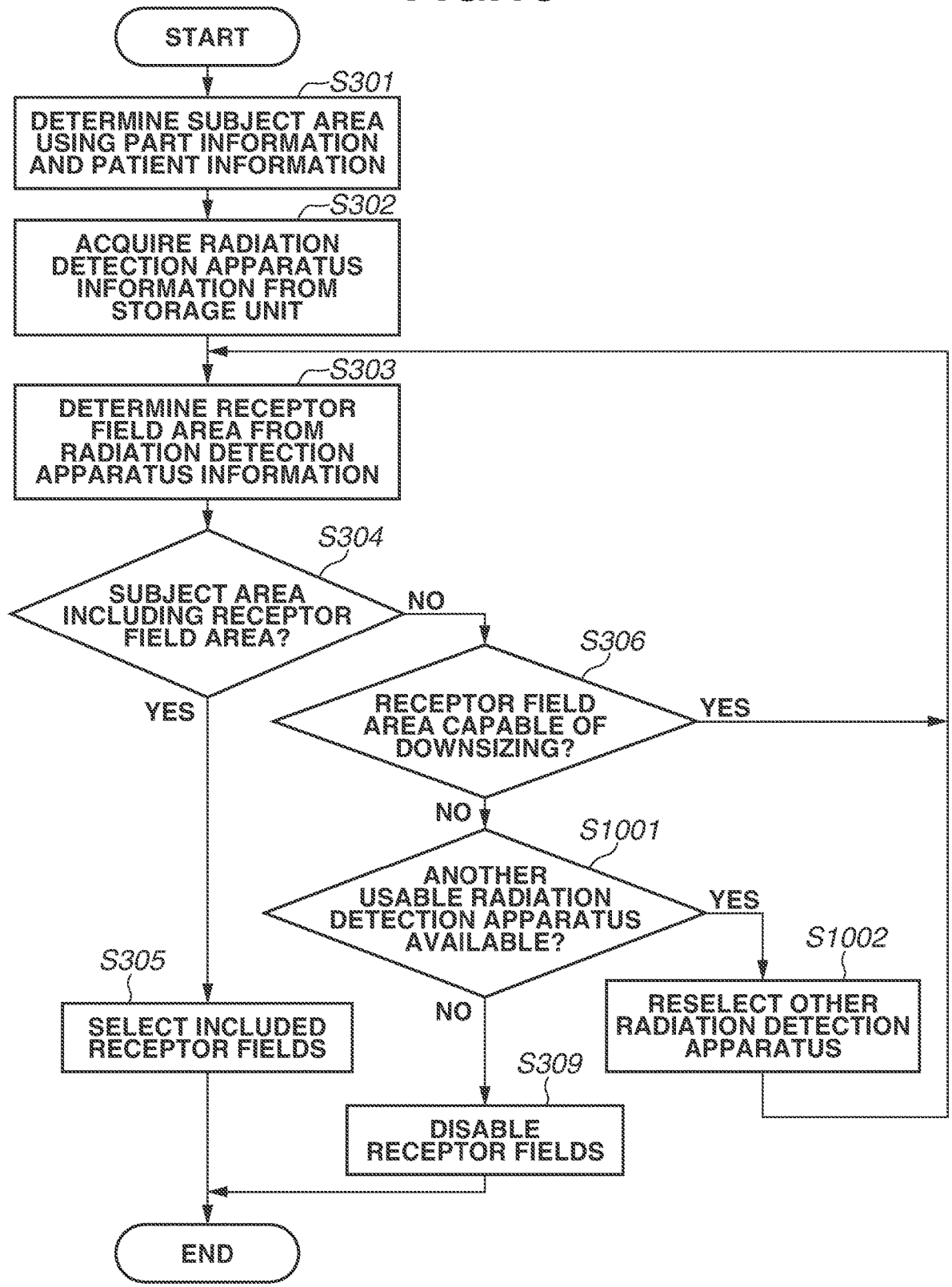
FIG. 10 is a flowchart related to a determination unit according to a third exemplary embodiment.

The process illustrated in the flowchart of FIG. 10 is performed during execution of step S203 in FIG. 6.

Step S306 and preceding steps are identical to those in the first exemplary embodiment and thus description thereof will be omitted. In the first exemplary embodiment, the receptor fields are disabled if it is determined in step S306 that there are no multiple receptor field areas and the receptor field area cannot be downsized.

In the present exemplary embodiment, however, in step S1001, it is determined whether any other types of radiation detection apparatuses besides the default radiation detection apparatus are registered and available. If there is any available radiation detection apparatus (YES in step S1001), notification is displayed to recommend the operator to switch to the different radiation apparatus, and the processing proceeds to step S1002. If there is no available radiation detection apparatus (NO in step S1001), the processing proceeds to step S309. Alternatively, in step S1001, notification may be provided to recommend the operator to set different receptor fields. Alternatively, notification may be displayed to recommend the operator to both switch to the different radiation detection apparatus and set the different receptor fields.

That is, if the receptor field area 502 cannot be downsized so as to eliminate a part of the receptor field area 502 not included in the subject area 501, the notification unit 108 displays a notification on the display unit to recommend at least one of the switching to the different radiation detection apparatus and the settings of the different receptor fields. Then, the operator performs processing based on the notification.

In step S1002, the operator selects the other notified radiation detection apparatus, and the processing proceeds to step S303. In step S303, a determination unit 104 determines the receptor field area again.

As a result of the process in the flowchart of FIG. 10, the appropriate combination of radiation detection apparatus and receptor fields is announced to the operator on the display unit 140 if there is any other combination than the default combination of radiation detection apparatus and receptor fields. Alternatively, the process in the flowchart of FIG. 10 may be invoked to provide a preliminary announcement to the operator when the inspection is selected in step S202.

As described above, the series of steps is executed by a radiographic imaging system 10.

According to the above description, the radiographic imaging system 10 according to the third exemplary embodiment can reduce the burden on the operator and improve the usability of the system by proposing a more appropriate combination of a radiation detection apparatus and receptor fields than the default combination of a radiation detection apparatus and receptor fields.

The present invention may be carried out by supplying programs for implementing one or more functions in the above-described exemplary embodiments to a system or apparatus via a network or storage medium, and causing one or more processors in the system or apparatus to read and execute the programs. In addition, the present invention may be carried out by circuits implementing the one or more functions.

The processors or circuits may include a central processing unit (CPU), a micro processing unit (MPU), a graphics processing unit (GPU), an application specific integrated circuit (ASIC), and a field programmable gateway (FPGA). The processors or circuits may include a digital signal processor (DSP), a data flow processor (DFP), or a neural processing unit (NPU).

The radiographic imaging system in each of the above-described exemplary embodiments may be implemented as a single apparatus or a plurality of apparatuses communicably combined to execute the above-described processes, which are both included as exemplary embodiments of the present invention. The above-described processes may be executed by a common server apparatus or server group. The plurality of apparatuses constituting the radiographic imaging system needs to be communicable with each other at a predetermined communication rate and is not required to present in the same facility or the same country.

The exemplary embodiments of the present invention include a mode of supplying software programs for implementing the functions in the above-described exemplary embodiments to a system or apparatus and causing a computer in the system or apparatus to read and execute codes of the supplied programs.

Since the computer implements the processes in the exemplary embodiments, the program codes installed in the computer therefore constitute one of exemplary embodiments of the present invention. In addition, based on instructions included in the programs read by the computer, an operating system (OS) running on the computer may perform some or all of the actual processes, so that the functions of the above-described exemplary embodiments can be implemented by the processes.

The present invention is not limited to the above-described exemplary embodiments and various modifications (including organic combinations of the exemplary embodiments), such as applications to still image capturing and moving image capturing, are possible based on the gist of the present invention, and these modifications are not excluded from the scope of the present invention.

That is, all configurations obtained by combining the above-described exemplary embodiments are included in exemplary embodiments of the present invention.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, it is possible to reduce the burden on the operator and improve the usability of the system.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-080613, filed May 11, 2021, which is hereby incorporated by reference herein in its entirety.

What is claimed is:

1. A control apparatus comprising:
a detection unit configured to detect switching between a plurality of radiation detection apparatuses, each of the plurality of radiation detection apparatuses being configured to capture a radiographic image through detection of radiation and including a plurality of receptor fields for performing automatic exposure control;
an acquisition unit configured to acquire information regarding one of the plurality of radiation detection apparatuses to be used for image capturing in a case where switching to the one of the plurality of radiation detection apparatuses has been detected; and
a selection unit configured to select one or more of the plurality of receptor fields of the one of the plurality of radiation detection apparatuses to be used for the image capturing based on the acquired information and information of a subject as an image capturing target and information of a part of the subject to be imaged.

2. The control apparatus according to claim 1, wherein the acquired information includes at least any one of a size of the one of the plurality of radiation detection apparatuses, a number of the plurality of receptor fields, positions of the plurality of receptor fields, a distance between two different receptor fields, and a size of the plurality of receptor fields.

3. The control apparatus according to claim 1, further comprising a determination unit configured to determine an inclusive relationship between a subject area that is determined using the information of the subject and the information of the part of the subject to be imaged, and a receptor field area that is determined using the information regarding the radiation detection apparatus and the information of the part of the subject to be imaged,
wherein the selection unit selects the one or more of the plurality of receptor fields based on the inclusive relationship between the subject area and the receptor field area determined by the determination unit.

4. The control apparatus according to claim 3, wherein if the determination unit determines that the subject area includes the whole of the receptor field area, the selection unit selects receptor fields set for the part of the subject to be imaged.

5. The control apparatus according to claim 3, wherein if the determination unit determines that the subject area does not include a part of the receptor field area, the determination unit further determines an inclusive relationship between a receptor field area obtained by downsizing the receptor field area to eliminate the part not included and the subject area.

6. The control apparatus according to claim 5, further comprising a setting unit configured to disable the receptor fields if the receptor field area cannot be downsized to eliminate the part not included.

7. The control apparatus according to claim 5, further comprising a notification unit configured to display on a display unit a notification to recommend switching to a different radiation detection apparatus if the receptor field area cannot be downsized to eliminate the part not included.

8. The control apparatus according to claim 3, wherein the determination unit compares the subject area and the receptor field area by overlapping at least any of a side of the subject area and a side of the receptor field area or a center of the subject area and a center of the receptor field area.

9. The control apparatus according to claim 1,
wherein the detection unit detects switching from a first radiation detection apparatus to a second radiation detection apparatus different from the first radiation detection apparatus in at least one of a number of the receptor fields and a size of the radiation detection apparatus, and
wherein the acquisition unit acquires information regarding the second radiation detection apparatus.

10. The control apparatus according to claim 9, wherein the selection unit selects the one or more receptor fields by comparing a subject area and a receptor field area that is determined based on setting information set for the first radiation detection apparatus through an operation unit.

11. A storage medium storing a program for causing a computer to execute functions of each unit of the control apparatus according to claim 1.

12. A control apparatus comprising:
a detection unit configured to detect switching between radiation detection apparatuses, the radiation detection apparatuses being configured to capture a radiographic image through detection of radiation and having receptor fields for performing automatic exposure control;
an acquisition unit configured to acquire information regarding a radiation detection apparatus to be used for image capturing, switching to the radiation detection apparatus having been detected; and
a determination unit configured to determine an inclusive relationship between a subject area that is inferred by inputting an optical image obtained by optically imaging a subject to a learned model that has undergone learning so as to identify a plurality of pixels constituting an optical image as a first class group and a receptor field area that is determined using information on the radiation detection apparatus and information on a part to be imaged; and a selection unit configured to select one or more receptor fields from the receptor fields based on an inclusive relationship between the subject area and the receptor field area determined by the determination unit.

13. A radiographic imaging system including a radiation generation apparatus configured to emit radiation, radiation detection apparatuses configured to capture a radiographic image through detection of the radiation and having receptor fields for performing automatic exposure control, and a control apparatus configured to communicate with the radiation detection apparatuses to perform operation control, the radiographic imaging system comprising:

a detection unit configured to detect switching between the radiation detection apparatuses;

an acquisition unit configured to acquire information regarding a radiation detection apparatus to be used for image capturing, switching to the radiation detection apparatus having been detected; and a selection unit configured to select one or more receptor fields from the receptor fields of the radiation detection apparatus to be used for the image capturing, based on acquired information regarding the radiation detection apparatus and information on a subject that is a target of image capturing and information on a part to be imaged.

14. A control method comprising:

detecting switching between radiation detection apparatuses, the radiation detection apparatuses being configured to capture a radiographic image through detection of radiation and having receptor fields for performing automatic exposure control;

acquiring information regarding a radiation detection apparatus to be used for image capturing, switching to the radiation detection apparatus having been detected; and selecting one or more receptor fields from the receptor fields of the radiation detection apparatus to be used for the image capturing, based on acquired information regarding the radiation detection apparatus and information on a subject that is a target of image capturing and information on a part to be imaged.

* * * * *